| United States Patent [19] | [11] Patent Number: 4,744,832 |
| Franz et al. | [45] Date of Patent: May 17, 1988 |

[54] IRON OXIDE COATED PERLESCENT PIGMENTS

[75] Inventors: Klaus D. Franz, Kelkheim; Klaus Ambrosius, Frankfurt am Main, both of Fed. Rep. of Germany

[73] Assignee: Merck Patent Gesellschaft mit beschrankter Haftung, Darmstadt, Fed. Rep. of Germany

[21] Appl. No.: 894,138

[22] Filed: Aug. 7, 1986

[30] Foreign Application Priority Data

Aug. 7, 1985 [DE] Fed. Rep. of Germany ....... 3528256

[51] Int. Cl.$^4$ .......................... C09C 1/24; C09C 1/36
[52] U.S. Cl. .................... 106/309; 106/291; 106/300; 106/304; 106/308 B; 428/324
[58] Field of Search .......... 106/291, 300, 304, 308 B, 106/309; 428/324

[56] References Cited

U.S. PATENT DOCUMENTS

| 3,087,828 | 4/1963 | Linton | 106/291 |
| 3,553,001 | 1/1971 | Kohlschutter . | |
| 3,711,308 | 1/1973 | Brand et al. | 106/308 B |
| 3,874,890 | 4/1975 | Bernhard et al. | 106/291 |
| 3,926,659 | 12/1975 | Bernhard et al. | 106/291 |
| 4,086,100 | 4/1978 | Esselborn et al. | 106/291 |
| 4,146,403 | 3/1979 | Armanini et al. | 106/291 |
| 4,499,143 | 2/1985 | Panush | 106/291 |
| 4,551,491 | 11/1985 | Panush | 106/304 |
| 4,552,593 | 11/1985 | Ostertag | 106/291 |
| 4,615,940 | 10/1986 | Panush et al. | 428/324 |

FOREIGN PATENT DOCUMENTS

| 208578 | 8/1979 | Czechoslovakia . |
| 2009566 | 6/1972 | Fed. Rep. of Germany . |
| 1359933 | 7/1974 | United Kingdom . |

*Primary Examiner*—Paul Lieberman
*Attorney, Agent, or Firm*—Millen and White

[57] ABSTRACT

The application relates to a pearlescent pigments based on platelet-like substrates, such as mica, which are coated with metal oxides, the metal oxide layer containing titanium and also iron, wherein the pigment has a multi-layer structure in which a first layer of $TiO_2$ in the rutile form is followed by a layer of pseudobrookite and an iron oxide layer.

16 Claims, No Drawings

IRON OXIDE COATED PERLESCENT PIGMENTS

BACKGROUND OF THE INVENTION

The invention relates to pearlescent pigments based on platelet-like substrates, e.g., mica, which are coated with metal oxides, the metal oxide layer containing both titanium and iron.

Iron-containing mica flake pigments have already been described in the art and have also been used successfully for many years. The pigments described include not only pigments in which iron oxide is precipitated onto the mica platelets together with another metal oxide, in particular titanium dioxide, but also pigments in which the precipitations are carried out in succession.

U.S. Pat. No. 3,087,828 describes obtaining, by means of precipitation of an $Fe_2O_3$ layer onto a $TiO_2$ layer, golden-colored pigments which take on a reddish hue after calcination. German Pat. No. 1,959,998, corresponding to U.S. Pat. No. 3,711,308, describes pigments which possess on mica an initial mixed layer of titanium oxide and iron oxide and thereon a top layer of titanium and/or zirconium dioxide.

German Pat. No. 2,244,298, corresponding to U.S. Pat. No. 3,874,890, describes a process for preparing golden-colored pearlescent pigments in which a $TiO_2$- and/or $ZrO_2$-coated mica pigment is first coated with iron(II) hydroxide, which is then oxidized to $Fe_2O_3$.

German Offenlegungsschrift No. 2,313,331, corresponding to U.S. Pat No. 3,926,659, describes advantageous iron-containing pigments in which the iron oxide is present in certain defined crystal modifications.

Also, German Offenlegungsschrift No. 2,723,871, corresponding to U.S. Pat. No. 4,146,403, describes mica pigments which have a thick $Fe_2O_3$ layer on a very thin $TiO_2$ or $Al_2O_3$ layer.

In all the cases described, $TiO_2$ is applied in the anatase form. However, on calcination of the pigment the precipitated iron oxide diffuses very strongly into the $TiO_2$ layer, so that even in those cases where initially separate layers of $TiO_2$ and $Fe_2O_3$ are precipitated, a mixed layer consisting essentially of pseudobrookite is present after the calcination.

German Pat. No. 2,522,572, corresponding to U.S. Pat. No. 4,086,100, has proposed providing mica pigments coated with $TiO_2$ in the rutile form with an additional top layer of coloring metal oxides, among which $Fe_2O_3$ is mentioned. With relatively law amounts of iron oxide in these coatings, it has been observed that on calcination the iron oxide diffuses to form a mixed layer of pseudobrookite on the rutile base.

By "a relatively low amount of iron oxide" is meant a content of iron oxide which is not substantially greater than about 5% by weight based on the total pigment weight.

SUMMARY OF THE INVENTION

It has now been found, surprisingly, that rutile and anatase differ substantially as relates to the diffusion of iron oxide during calcination. While in the case of anatase even large amounts of iron oxide will virtually completely diffuse into the $TiO_2$ layer during calcination to form pseudobrookite, it has been found that in the case of a rutile layer, the rate of diffusion is so low that only a relatively thin pseudobrookite layer forms on the rutile layer, while the remainder of the precipitated iron oxide is actually present in the form of $Fe_2O_3$.

Indeed, in the case of the new pigments, which are distinctly improved as regards luster and stability, it is possible, in contrast to the prior art pigments where the iron oxide layer is precipitated onto an anatase layer, to use X-ray diffraction to detect adjacent discrete phases of rutile $TiO_2$ and of $Fe_2O_3$.

Surprisingly, pigments having such a 3-layer structure possess not only distinctly improved color characteristics (improved tinctorial strength and brilliance and improved hiding power) but also an improved chemical stability for example, with respect to photoactivity or as smelting fluxes for glazings and enamel.

The invention, therefore, provides in pearlescent pigments based on platelet-like substrates, especially mica substrates, which are coated with metal oxides, the metal oxide layer containing titanium and also iron, the improvement wherein the pigment has a multilayer structure in which a first layer of $TiO_2$ in the rutile form is covered with a layer of pseudobrookite which in turn, is covered by an iron oxide layer.

The invention, in a process aspect, involves a process for preparing pearlescent pigments by coating platelet-like substrates such as mica with an iron- and titanium-containing metal oxide layer, the improvement wherein first a titanium dioxide or titanium dioxide hydrate layer is precipitated thereon, the precipitation being effected in a manner known wherein a rutile layer is formed on calcination, and in that either before or after calcination of this pigment an iron oxide or hydroxide layer is precipitated thereon. The pigment is thereafter calcined.

DETAILED DESCRIPTION

It is critical in the present invention that the $TiO_2$ layer is applied in such a way that the rutile structure is formed on calcination. This can be effected, e.g., by one of the known methods, in which foreign ions, in particular tin (IV), are incorporated into the layer. These methods are described, e.g., in German Pat. No. 2,214,545 and the aforementioned U.S. Pat. No. 4,086,100 rutilization being forced by incorporating tin dioxide close to the mica or in discrete layers between the $TiO_2$. However, there are other known methods, such as, for example, the incorporation of zinc oxide in accordance with Czech Pat. No. 208,578 or the incorporation of iron(III) into the $TiO_2$ layer in accordance with German Pat. No. 1,959,998, corresponding to U.S. Pat. No. 3,711,308, which also lead to rutile layers which can be utilized within the context of the present invention.

There are essentially two known processes for precipitating the $TiO_2$ layer. In one, the precipitation can be effected as described in U.S. Pat. No. 3,087,828 by addition of a sulfuric acid titanyl sulfate solution to the mica suspension and hydrolysis thereof by heating to about 100° C., the layer thickness and the associated interference color being initially predetermined by the amount of titanyl sulfate present. However, the precipitation can also be carried out as described in German Pat. No. 2,009,566, wherein an aqueous titanium salt solution is gradually added to a hot mica suspension at about 50°–100° C., preferably 70°–80° C., and by the simultaneous addition of a suitable base, for example, an aqueous ammonia solution of an aqueous alkali metal hydroxide solution, a substantially constant pH value of about 0.5–5, in particular, about 1.5–2.5, being maintained. As soon as the desired layer thickness of the $TiO_2$ precipitate is reached, the addition of the titanium salt solution is stopped.

To obtain the titanium dioxide layer in the desired rutile structure, the precipitation is modified in the known manner so that either a tin salt is present in the mica suspension and is hydrolyzed together with the titanyl sulphate, or that after the precipitation of a thin $TiO_2$ layer, an $SnO_2$ intermediate layer and then an additional $TiO_2$ layer are precipitated thereon, it being possible to repeat these alternating precipitations several times, as required.

The iron oxide layer can also be precipitated thereon by known methods. In this aspect it is possible to start not only from iron(III) salts, as described, for example, in German Pat. No. 1,467,468, but also from iron(II) salts, as described in U.S. Pat. No. 3,874,890; the initially formed coating of iron(II) hydroxide is oxidized to iron(III) oxide hydrate.

Precipitation of the iron oxide layer can be effected not only onto a calcined and, hence, already rutilized $TiO_2$ layer, but also directly after the $TiO_2$ precipitation onto the uncalcined pigment. In the latter case, the subsequent calcination is surprisingly accompanied by a very low diffusion of the iron into the $TiO_2$ layer, although relatively high temperatures of about 700° to about 950° C., preferably about 800° to about 900° C., are used in the calcination, and the conventional calcination times of about 10 to 200, preferably 20 to 100, minutes are used.

Since even when utilizing the rutile $TiO_2$ substrate taught herein, a small amount of diffusion of iron oxide into the $TiO_2$ layer with an accompanying formation of pseudobrookite cannot be completely avoided, the $TiO_2$ layer should have a certain minimum thickness of about 40 nm, so as to produce a 3-layer structure of $TiO_2$/pseudobrookite/$Fe_2O_3$. In general, the layer thicknesses of the $TiO_2$ layer before calcination range from about 40 to about 200 nm and preferably, thicknesses of about 40 to about 150 nm are preferred. It is also preferred that the titanium content, calculated as $TiO_2$, relative to the total pigment is about 20-50% by weight.

An essential feature of the 3-layer structure taught herein is the particular layer thickness of the precipitated $Fe_2O_3$. This thickness should always be sufficiently large so that after the calcination and the resulting formation of an intermediate layer of pseudobrookite a pure $Fe_2O_3$ layer still remains on the surface of the pigment particles. For that reason the $Fe_2O_3$ layer precipitated is at least about 15 nm thick and preferably has a thickness of about 15 to about 50 nm, most preferably about 20 to about 40 nm. The iron content calculated as $Fe_2O_3$, relative to the total pigment as a rule is about 10-50% by weight. Iron oxide contents of at least 15% by weight are preferred.

It is also possible to incorporate a variety of dopants, in particular other colored or colorless metal oxides, not only into the $TiO_2$, but also into the $Fe_2O_3$ layer. Suitable dopants include compounds of aluminum(III), silicon(IV), zirconium(IV), chromium(III), boron(III) and phosphorus(V). These dopants are each incorporated, where appropriate, in amounts of about 0 to 2% by weight. However, total amounts of about 2% in case only one or two dopants are used and in case the dopants are incorporated in the $TiO_2$ layer, to about 5% by weight in case more than two dopants are used or the dopants are incorporated in the iron oxide layer, should not be exceeded. Larger amounts of dopants are on the one hand not necessary and show on the other hand a tendency to influence negatively the quality of the pigments.

If dopants are to be incorporated in one or even all of the layers, they can be added either to the mica suspension, to one of the added salt solutions, or where appropriate, to the added base in the form of water-soluble salts. The dopants are generally homogeneously distributed in the metal oxide layer(s). However, it is also possible and may be advantageous to effect such an enrichment either close to the mica or at the surface of the pigment.

It is also possible to subject the pigment to a subsequent coating or treatment which further increases its light, weather or chemical stability or facilitates the handling of the pigment, particularly regarding the incorporation of it into various media. Representative aftercoatings or aftertreatments include the methods described in German Pat. No. 2,215,191, German Offenlegungsschrift Nos. 3,151,354, 3,235,017 and 3,334,598. Owing to the fact that even without these additional measures the pigments fabricated according to the teachings of the invention have excellent properties, these optionally applied substances only account for about 0 to 5, and preferably about 0 to 3% by weight of the total pigment.

The pigments of the invention can be used like the hitherto disclosed pigments; for example, for pigmenting plastics, inks, paints, body care agents and cosmetics, as well as owing to their high chemical stability they also can be used in smelting fluxes for glazes and enamel.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLE 1

In accordance with Example 1A of German Pat. No. 2,214,545, 100 g of mica are coated in succession with 0.8 g of $SnO_2$ and 30 g of $TiO_2$ in aqueous suspension. The suspended uncalcined pigment exhibits a slightly yellow interference color. After switching off the stirrer and allowing the pigment to settle out, the supernatant liquor is drawn off, the 2500 ml of water, 81 g of anhydrous $FeCl_3$ and 16 g of sodium acetate are added. One hour of heating at 70°-80° C. is followed by filtration, washing until chloride-free, drying, and calcination at 850° C. for 30 min. The result obtained is a pigment having a very dark golden pigment and interference color, the X-ray diffraction values of which (Debye-Scherrer diagram) reveal that discrete layers of rutile, pseudobrookite and haematite are present on the muscovite.

The pigment is very stable in glazes and exhibits no photoactivity in the Kronos test.

COMPARATIVE EXAMPLE 1A

Example 1 is repeated, except without the $SnO_2$ precipitation. The result obtained is a pigment with a bright yellow pigment and yellow interference color, the coating of which consists of anatase and pseudobrookite, according to the X-ray diffraction values. The stability of the pigment in glazes is poor, and in the Kronos test it exhibits photoactivity.

EXAMPLE 2

In accordance with Example 2 of German Pat. No. 2,522,572, corresponding to U.S. Pat. No. 4,086,100, 109 g of a pigment having a blue interference color are prepared by alternately coating mica with $TiO_2$, $SnO_2$ and $TiO_2$. The settling out of the pigment is followed by decanting and addition of 2500 ml of water. To the suspension which has been heated to 75° C. and brought to a pH 6-7 with ammonia being gradually added, while air is blown in at the same time, a solution of 120 g of $FeSO_4.7H_2O$ in 400 ml of water and 1.5 ml of concentrated sulphuric acid is added, with the pH value being largely maintained constant by simultaneous addition of ammonia. The pigment is then separated off, washed until sulphate-free and dried and calcined at 850° C. for 30 min. The result obtained is a golden, lustrous pigment having a green interference color, and high hiding power, which, on the basis of the X-ray diffraction values, possesses layers of rutile, pseudobrookite and haematite It exhibits high stability in glazes and no photoactivity in the Kronos test.

COMPARATIVE EXAMPLE 2A

Example 2 is repeated, except that the $SnO_2$ intermediate layer is left out. The result obtained is a pigment having a bright yellow pigment and green interference color, which according to the X-ray diffraction values carries a coating of anatase and pseudobrookite. It exhibits poor stability in glazes and photoactivity in the Kronos test.

EXAMPLE 3

In accordance with the process of Example 1 of German Pat. No. 1,959,998, a mixed precipitate of hydrated titanium dioxide and hydrogenated iron(III) oxide is applied to 100 g of mica in aqueous suspension. As soon as an orange-colored interference is obtained, the pigment is allowed to settle out, the supernatant liquor is decanted off, and water is added to bring the volume to 2500 ml. Thereafter iron oxide is preciptiated, on as described in Example 2, again using 120 g of $FeSO_4.7H_2O$. Working up and calcination as in Example 2 gives a copper-colored pigment with a blue interference color and high stability, which shows rutile, pseudobrookite and haematite in the X-ray diffraction digram. It possesses high stability in glazes and no photoactivity in the Kronos test.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a pearlescent pigment comprising a plateletlike substrate coated with metal oxides, the metal oxide layer containing titanium dioxide and iron oxide, the improvement wherein the pigment comprises a multilayer structure in which superimposed on the substrate is a first layer of $TiO_2$ in the rutile form, formed from a precipitated layer of titanium dioxide or titanium dioxide hydrate, having a thickness of at least 40 nm, the latter being superimposed by a layer of pseudobrookite and the latter being superimposed by an iron oxide layer, formed by the precipitation of an iron oxide or hydroxide layer, having a thickness of at least 15 nm, wherein the $TiO_2$ concentration, relative to the total pigment, is about 20 to about 50% by weight, and the iron side concentration relative to the total pigment, is about 10 to about 50% by weight.

2. A pearlescent pigment according to claim 1, wherein the substrate is mica.

3. A pearlescent pigment according to claim 1, wherein dopants which are selected from compounds of aluminum(III), silicon(IV), zirconium(IV), chromium(III), boron(III) and phosphorous(V) are incorporated into at least one of the $TiO_2$ and $Fe_2O_3$ layers, said copants being present in a total of not more than about 5% by weight based on the pigment.

4. In a process for preparing pearlescent pigments by coating platelet-like substrates with an iron- and titanium-containing metal oxide layer, the improvement comprising first precipitating a titanium dioxide or titanium dioxide hydrate layer having a thickness of at least 40 nm and a concentration relative to the total pigment of about 20-50% by weight, said layer being calcinable to form a rutile layer, and before or after calcination of resultant pigment, precipitating an iron oxide or hydroxide layer having a thickness of at least 15 nm, and a concentration relative to the total pigment of about 10-50% by weight on the titanium dioxide or the titanium dioxide hydrate layer, and calcining the pigment.

5. A process according to claim 4, the step of precipitating said layer calcinable to rutile comprises precipitation of a $TiO_2$ layer, an $SnO_2$ intermediate layer and then an additional $TiO_2$ layer onto the platelet-like substrate.

6. A process according to claim 4, wherein the calcination occurs at about 700° to 950° C.

7. A process according to claim 4, wherein the $TiO_2$ layer is about 40 to about 200 nm.

8. A process according to claim 4, wherin the $TiO_2$ layer is about 40 to about 200 nm.

9. A process according to claim 8, wherein the iron oxide layer has a thickness of about 20 to 40 nm.

10. A process according to claim 4, wherein the iron oxide is precipitated onto an uncalcined titanium dioxide or titanium dioxide hydrate layer.

11. A process according to claim 4, wherein the titanium dioxide or titanium dioxide hydrate layer has a thickness of about 40-150 nm.

12. A process according to claim 4, wherein the iron oxide is $Fe_2O_3$ and the $Fe_2O_3$ layer has a thickness of about 15-50 nm.

13. A process according to claim 12, wherein the $Fe_2O_3$ layer has a thickness of about 20-40 nm.

14. A perlescent pigment according to claim 1, wherein the iron oxide concentration, relative to the total pigment, is 15-50% by weight.

15. A process according to claim 4, wherein the iron oxide concentration, relative to the total pigment, is 10-50% by weight.

16. A process according to claim 4, wherein the iron oxide concentration, relative to the total pigment, is about 15-50% by weight.

* * * * *